United States Patent [19]
Hart et al.

[11] Patent Number: 6,017,348
[45] Date of Patent: *Jan. 25, 2000

[54] APPARATUS AND METHODS FOR ARTICULAR CARTILAGE DEFECT REPAIR

[75] Inventors: Rickey D. Hart, Plainville, Mass.; F. Alan Barber, Frisco, Tex.; James C. Chow, Mount Vernon, Ill.

[73] Assignee: Innovasive Devices, Inc., Marlborough, Mass.

[*] Notice: This patent is subject to a terminal disclaimer.

[21] Appl. No.: 08/866,830

[22] Filed: May 30, 1997

Related U.S. Application Data

[63] Continuation-in-part of application No. 08/399,428, Mar. 7, 1995, Pat. No. 5,782,835.

[51] Int. Cl.⁷ .................................................. A61B 17/00
[52] U.S. Cl. ........................... 606/79; 606/179; 606/88
[58] Field of Search .................................. 606/80, 79, 96, 606/88, 86, 167, 179, 180, 184

[56] References Cited

U.S. PATENT DOCUMENTS

| Re. 34,293 | 6/1993 | Goble et al. . |
|---|---|---|
| 3,577,979 | 5/1971 | van der Gaast . |
| 3,848,601 | 11/1974 | Ma et al. . |
| 4,059,115 | 11/1977 | Jumashev et al. . |
| 4,142,517 | 3/1979 | Stavropoulos et al. . |
| 4,293,962 | 10/1981 | Fuson . |
| 4,375,259 | 3/1983 | Mancini et al. . |
| 4,408,938 | 10/1983 | Maguire . |
| 4,559,936 | 12/1985 | Hill . |
| 4,627,853 | 12/1986 | Campbell et al. . |
| 4,649,918 | 3/1987 | Pegg et al. ................................ 606/79 |
| 4,782,833 | 11/1988 | Einhorn et al. . |
| 4,798,213 | 1/1989 | Doppelt . |
| 4,871,289 | 10/1989 | Choiniere . |
| 4,873,991 | 10/1989 | Skinner . |

(List continued on next page.)

FOREIGN PATENT DOCUMENTS

| 0530804 | 10/1993 | European Pat. Off. . |
|---|---|---|
| 8601068 | 4/1986 | Germany . |
| 9312792 | 10/1993 | Germany . |
| 1454423 A1 | 1/1989 | U.S.S.R. . |
| WO 93/07819 | 4/1993 | WIPO . |
| WO 83/02553 | 8/1993 | WIPO . |

OTHER PUBLICATIONS

Case Report, "Arthroscopic Multiple Osteochondral Transplantation to the Chrondal Defect in the Knee Associated with Anterior Cruciate Ligament Disruption" by Yoshitaka Matsusue, M.D., Takao Yamamuro, M.D. and Hiromichi Hama, M.D., pp. 318–322 from Arthroscopy: *The Journal of Arthroscopic and Related Surgery* 9(3):318–521, Published by Raven Press, Ltd. (1993).

(List continued on next page.)

*Primary Examiner*—Michael Buiz
*Assistant Examiner*—David O. Reip
*Attorney, Agent, or Firm*—Choate, Hall & Stewart

[57] ABSTRACT

A bone plug removal and emplacement tool includes a cylindrical cutting element having a proximal cutting edge and a cutting tooth. The outer surface of the cutting element can include an integral shoulder (e.g., in lieu of a replaceable outer sheath) that is spaced-apart from the proximal cutting edge and that engages the surface of the bone to define a depth stop for the cutting edge. An additional cylindrical element can be disposed within the cutting element. The proximal end of that additional element, which is referred to as a "harvester," is substantially aligned with the proximal end of the cutting element to receive a plug cut from the bone. The harvester can be slidably withdrawn from the cutting element to facilitate transplating the bone plug at another location. For this purpose, a stem or plunger can be slidably inserted and moved in the harvester to dislodge the plug.

24 Claims, 14 Drawing Sheets

U.S. PATENT DOCUMENTS

| | | |
|---|---|---|
| 4,884,572 | 12/1989 | Bays et al. . |
| 5,067,964 | 11/1991 | Richmond et al. . |
| 5,092,891 | 3/1992 | Kummer et al. . |
| 5,116,337 | 5/1992 | Johnson . |
| 5,139,520 | 8/1992 | Rosenberg . |
| 5,152,763 | 10/1992 | Johnson . |
| 5,169,401 | 12/1992 | Lester et al. . |
| 5,190,548 | 3/1993 | Davis . |
| 5,224,946 | 7/1993 | Hyhurst et al. . |
| 5,234,435 | 8/1993 | Seagrave, Jr. . |
| 5,236,445 | 8/1993 | Hayhurst et al. . |
| 5,268,001 | 12/1993 | Nicholson et al. . |
| 5,269,785 | 12/1993 | Bonutti . |
| 5,324,300 | 6/1994 | Elias et al. . |
| 5,341,816 | 8/1994 | Allen . |
| 5,382,250 | 1/1995 | Kraus . |
| 5,417,712 | 5/1995 | Whittaker et al. . |
| 5,423,824 | 6/1995 | Akerfeldt et al. . |
| 5,458,601 | 10/1995 | Young, Jr. et al. . |
| 5,464,427 | 11/1995 | Curtis et al. . |
| 5,472,452 | 12/1995 | Trott . |
| 5,480,403 | 1/1996 | Lee et al. . |
| 5,486,197 | 1/1996 | Le et al. . |
| 5,489,210 | 2/1996 | Hanosh . |
| 5,490,853 | 2/1996 | Burkinshaw et al. ............... 606/79 |
| 5,496,326 | 3/1996 | Johnson . |
| 5,501,683 | 3/1996 | Trott . |
| 5,501,695 | 3/1996 | Anspach et al. . |
| 5,515,861 | 5/1996 | Smith . |
| 5,522,845 | 6/1996 | Wenstrom, Jr. . |
| 5,545,180 | 8/1996 | Le et al. . |
| 5,571,104 | 11/1996 | Li . |
| 5,632,747 | 5/1997 | Scarborough et al. ............... 606/79 |
| 5,697,935 | 12/1997 | Moran et al. ............... 606/104 |

OTHER PUBLICATIONS

Smith & Nephew Endoscopy, MosaicPlasty™ Osteochondral Grafting Technique Guide, As described by: László Hangody, M.D., Ph.D., Gary Kish, M.D., Undated.

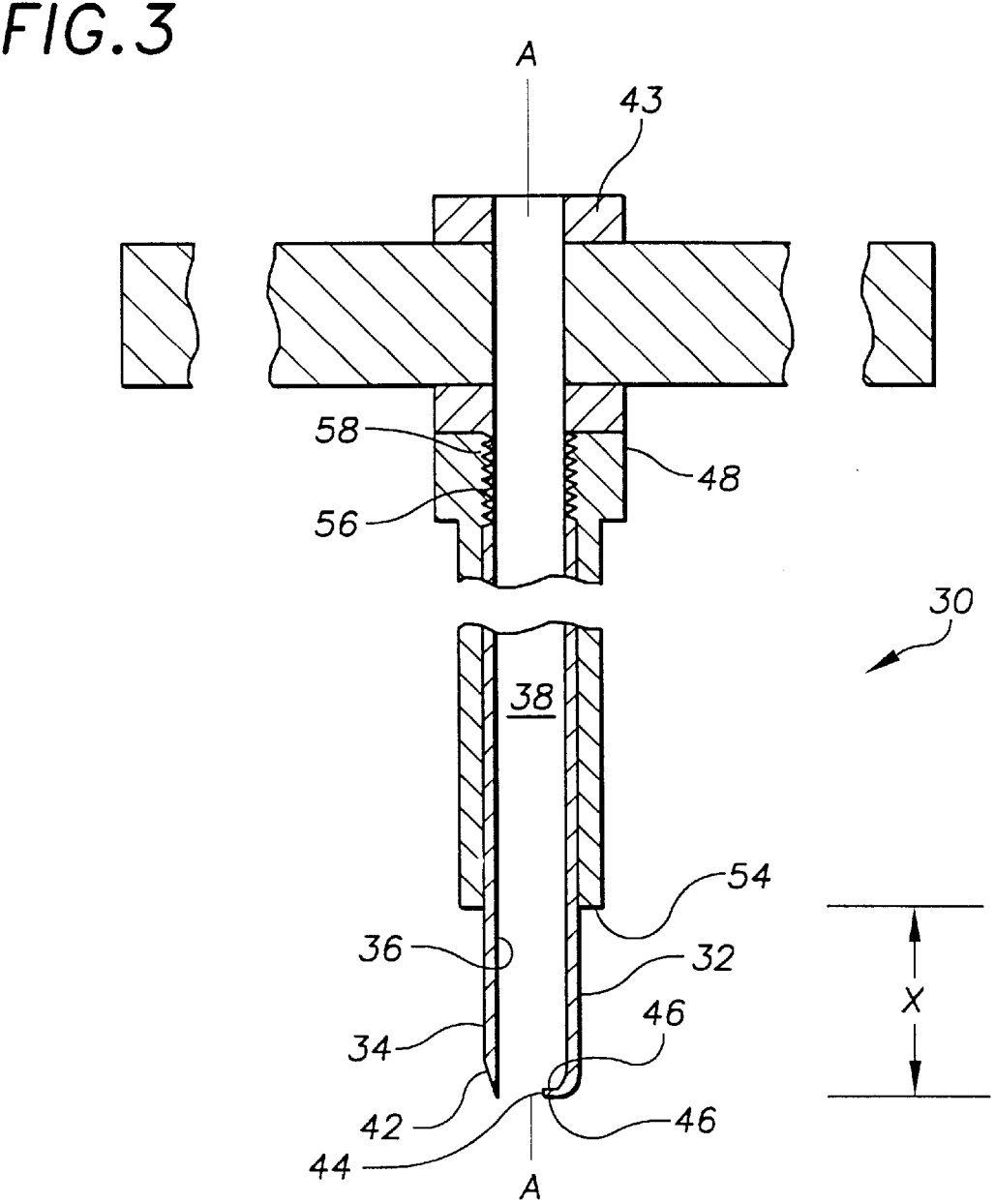

APPARATUS AND METHODS FOR ARTICULAR CARTILAGE DEFECT REPAIR

REFERENCE TO RELATED APPLICATIONS

This application is a continuation in part of, commonly assigned U.S. patent application Ser. No. 08/399,428 filed Mar. 7, 1995 now U.S. Pat. No. 5,782,835, the teachings of which are incorporated herein by reference.

BACKGROUND OF THE INVENTION

This invention relates to articular cartilage defects and their repair and more particularly to apparatus and methods for effecting such repair.

Defects in articular cartilage associated with trauma and osteochondritis dissecans represent a difficult challenge for surgeons. The patient can expect to face progressive deterioration over time leading to advanced osteochondritis, arthritis and the possibility of joint replacement. The knee as a weight-bearing joint is particularly susceptible to this problem, although similar injuries to the articular cartilage of other joints in humans and other mammals also occur with regularity.

FIG. 1 illustrates a knee joint 10 between the distal end 11 (i.e., that surface farthest from the center of the body) of a femur 12 and the proximal end 13 (i.e., that surface closest to the center of the body) of the tibia 14. Portions 15, 17 of the connective tissue which movably ties the femur 12 to the underlying tibia 14 and fibula 18 are shown. Normally interposed between opposing surfaces of the femur 12 and tibia 14 are lateral and medial meniscus cartilages, 21 and 23, respectively. The condyles 22 at the distal end 11 of the femur 12 are normally supported by the meniscus cartilages 21 and 23 on the proximal end 13 of the tibia 14. Normally, the distal end 11 of femur 12, including the condyles 22 is covered by a layer 28 of cartilaginous material about 5 mm thick, referred to as the articular cartilage. Articular cartilage 28 forms a generally resilient pad which is fixed on the distal surface 11 of the femur 12 to protect the femur from wear and mechanical shock. The articular cartilage 28, when lubricated by fluid in the knee joint 10, provides a surface which is readily slidable on the underlying surfaces of the meniscus cartilages 21 and 23 or on the proximal surface 13 of the tibia 14 if one or both of the meniscus cartilages 21, 23 should be partially or totally absent. Nevertheless, the articular cartilage 28 may become damaged in that it may be torn 24 or holed or become excessively worn.

Methods have been used to repair such articular cartilage damage before it can spread or result in eventual injury or wear to the underlying condyles 22, meniscus cartilages 21, 23, or tissues associated with the tibia 12. It has been known to replace damaged articular cartilage with a layer of fibrous material. See U.S. Pat. No. 5,067,964. Repairing defects in articular cartilage in human or other mammalian joints therefore requires materials that have been approved by the FDA for use in the human body. Is often problematic to find such materials that are commercially available and relatively low in cost in which completion of the repairs are within the skills of qualified orthopedic surgeons. Another repair method involves packing an articular cartilage defect with bits of cancellous and cortical bone (Soviet Patent SU 1454423, Jun. 27, 1986) that have been chipped from defect-free bone. This latter technique avoids using foreign materials but, like the former methods, does not preserve the original orientation of bone and cartilage.

Prostheses have also been used for replacement of the joint itself. Problems encountered after implanting such prostheses are usually caused by the cements used to attach the prostheses to the host bone. Further, some prostheses associated with joint replacements are actually much larger than the degenerated tissue that needs to be replaced so that extensive portions of healthy bone are typically removed to accommodate the prostheses.

The need remains to develop apparatus and methods which are suitable for articular cartilage repair and which avoid problems associated with prior art methods, such as those discussed above.

SUMMARY OF THE INVENTION

The present invention is an apparatus for repairing articular cartilage defects, and methods of using the apparatus, that harvest and utilize intact bone and intact articular cartilage plugs that preserve the natural orientation of the bone and articular cartilage.

One embodiment of the invention is a bone plug removal tool that includes a cylindrical cutting element having an external surface and having an internal surface defining an internal bore extending along a longitudinal axis of the cutting element from a proximal cutting edge. A cutting tooth is engaged with the internal surface at the proximal cutting edge and extends into the internal bore. The tooth is substantially orthogonal to the longitudinal axis of the cutting element and is defined between orthogonally extending surfaces disposed in parallel. A replaceable outer cylindrical sheath is arranged concentrically around the external surface of the cylindrical cutting element. The sheath also has an internal surface defining an internal bore extending along a longitudinal axis of the sheath. The sheath has a proximal terminus that is spaced-apart from the proximal cutting edge of the cylindrical cutting element and the terminus is designed to engage a surface of the bone to define a depth stop for the cutting edge. In preferred embodiments, the cutting tooth is a single tooth and screw threads are disposed on the external surface of the cylindrical cutting element for mating with corresponding screw threads on the internal surface of the cylindrical sheath. A handle may be engaged with a distal end of the tool for turning the tool into the bone once it has been driven to the desired depth. Thus, one aspect of the invention is a bone plug remover having an elongated body including two concentric elements in which an inner element is a cutting element and an outer element is replaceable and defines a depth stop for cutting.

Another embodiment of the invention is a bone plug emplacement tool to be used in conjunction with the bone plug removal tool. The preferred emplacement tool includes a cylindrical element having an internal surface defining an internal bore extending along a longitudinal axis of the element from a proximal end. The internal surface further defines an internal step adjacent a distal end of the element. A stem is disposed for co-axial movement within the element, the stem having a proximal end disposed within the internal bore. A shoulder is defined in the stem for mating engagement with the internal distal step of the element in order to limit distal movement of the stem within the internal bore. The proximal end of the stem, at the limit of distal movement, is spaced-apart from the proximal end of the co-axial element, the respective proximal ends defining between them an internal bone plug receiving space for receiving a bone plug of a certain length. The stem may be moved from a distal position, where the shoulder and step are engaged and the respective proximal ends define the space for receiving a bone plug, to a proximal position, where the stem is moved proximally within the internal bore and the bone plug is driven from the internal bone plug receiving space. A second step may be defined in the stem for limiting proximal movement. This second step is located distal to the first step and external to the cylindrical element. It is preferred that, in the distal position, the second step and the distal end of the element are at a distance from each other that is equal to, or less than, the length of the bone plug.

A further embodiment is a kit incorporating the various tools. The kit for repair of an articular cartilage includes the bone plug removal tool of the invention, an elongated plunger for insertion into the proximal end of the cutting element and for coaxial movement within it, the plunger for displacing a bone plug from the distal end of the cutting element and the bone plug emplacement tool of the invention. Kits may also include a drill bit containing a depth stop for removing a portion of damaged articular cartilage.

A further embodiment of the invention also includes the combination of the bone plug emplacement tool of the invention and an excised bone plug contained within the internal bone plug receiving space of the emplacement tool.

In yet another embodiment, the invention provides a bone plug removal and emplacement tool that includes a cylindrical cutting element having a proximal cutting edge and a cutting tooth, as described above. The outer surface of the cutting element can include an integral shoulder (e.g., in lieu of a replaceable outer sheath) that is spaced-apart from the proximal cutting edge and that engages the surface of the bone to define a depth stop for the cutting edge.

An additional cylindrical element can be disposed within the cutting element. The proximal end of that additional element, which is referred to as a "harvester," is substantially aligned with the proximal end of the cutting element to receive a plug cut from the bone. The harvester can be slidably withdrawn from the cutting element to facilitate transplanting the bone plug at another location. For this purpose, a stem or plunger can be slidably inserted and moved in the harvester to dislodge the plug.

The invention also pertains to a method of repairing a defective articular cartilage. The method includes the steps of removing a section of defective articular cartilage from a site of cartilage damage and forming a hole of sufficient depth to penetrate bone underlying the site of defective articular cartilage. Next, a bone plug comprising intact bone and intact articular cartilage adhering thereto is removed from a bone lacking defective articular cartilage and is placed into the hole at the site of articular cartilage damage, so that the intact articular cartilage of the bone plug is co-extensive, and in lateral registration (i.e., aligned) with, articular cartilage external to the bone hole at the site of cartilage damage. The term "intact" in this context means that the bone and overlying articular cartilage undergo minimal physical disturbance during the removal process.

BRIEF DESCRIPTION OF THE DRAWINGS

Other objects and purposes of the invention will be apparent to persons knowledgeable in this art upon reading the following description and inspecting the accompanying drawings which show:

FIG. 3 is the bone plug removal tool of FIG. 2 with the cylindrical sheath and cylindrical cutting element joined.

FIG. 8A is a cross section through a bone that contains a defect in the articular cartilage.

FIG. 8B is a cross section through a bone whose defective cartilage area has been removed and into which a bone hole has been drilled. A bone plug is illustrated in proper orientation for insertion.

FIG. 8C illustrates a bone plug received within a drilled bone hole.

FIG. 8D illustrates a plurality of drilled bone holes within an articular cartilage defect.

DETAILED DESCRIPTION OF THE INVENTION

Figure 1:
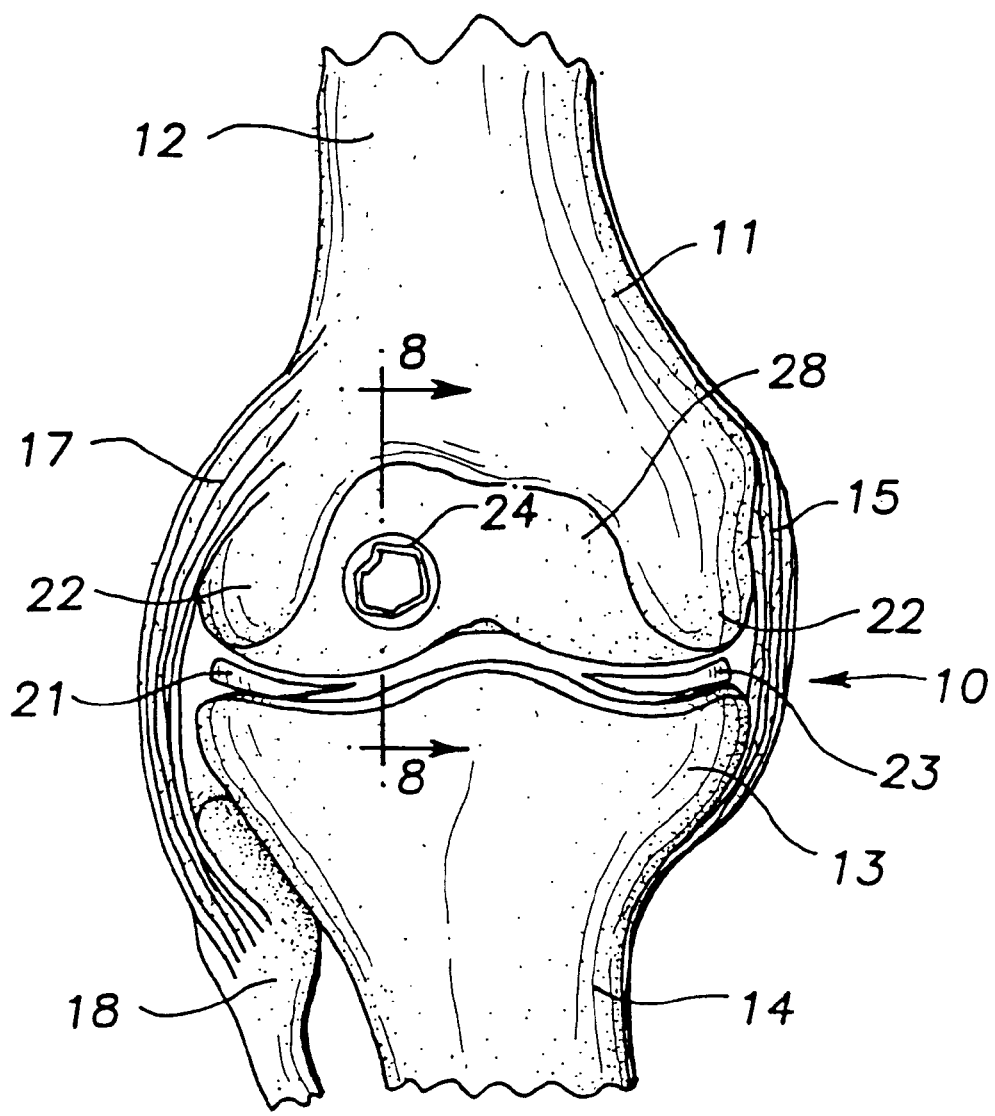
FIG. 1 is a fragmentary front elevation view of a human knee joint with sufficient tissue removed to show the articular cartilage on the condyles of the femur, and further showing a damaged area in the articular cartilage.
Figure 2:
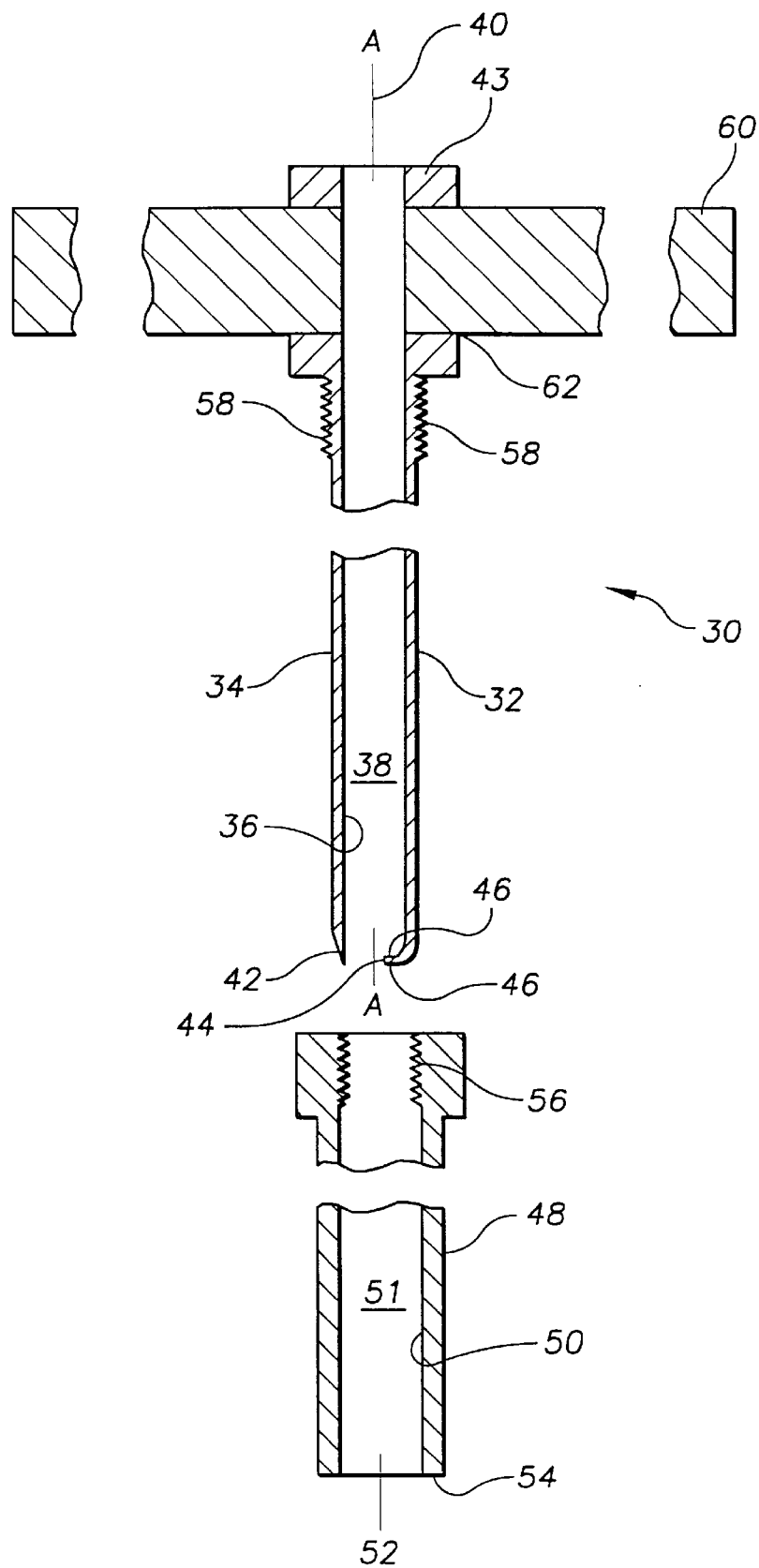
FIG. 2 is an exploded cross sectional view of a bone plug removal tool of the present invention.

Reference is now made to FIGS. 2–3 which illustrate one embodiment of the present bone plug removal tool. The bone plug removal tool 30 is a substantially cylindrical device made out of two pieces of surgical stainless steel. The tool 30 is formed into a cylindrical cutting element 32 and a cylindrical sheath 48 that is arranged concentrically around the cylindrical cutting element 32. Cutting element 32 has an external surface 34 and an internal surface 36. The internal surface 36 further defines an internal bore 38 extending along a longitudinal axis 40 (arrows A—A) of the cylindrical cutting element 32. The bore 38 extends distally away from a proximal cutting edge 42. In the present context, the term "proximal" refers to those portions of the apparatus that are closest to the center of the body or, alternately, are furthest away from the operator of the apparatus. The term "distal" refers to those portions of the apparatus that are furthest from the center of the body or, alternately, are closest to the operator of the apparatus. The internal bore 38 extends from the proximal cutting edge 42 to the distal end 43 of the cylindrical cutting element 32 from which a bone plug can be removed by the operator after bone plug extraction has been completed.

The proximal cutting edge 42 is sharpened so that any bone entering the internal bore 38 is cut from the surrounding bone. An excised bone plug trapped within bore 38 can move freely into this space and out the distal end 43 after the plug excision procedure has been completed, as discussed in more detail below.

Figure 4A:
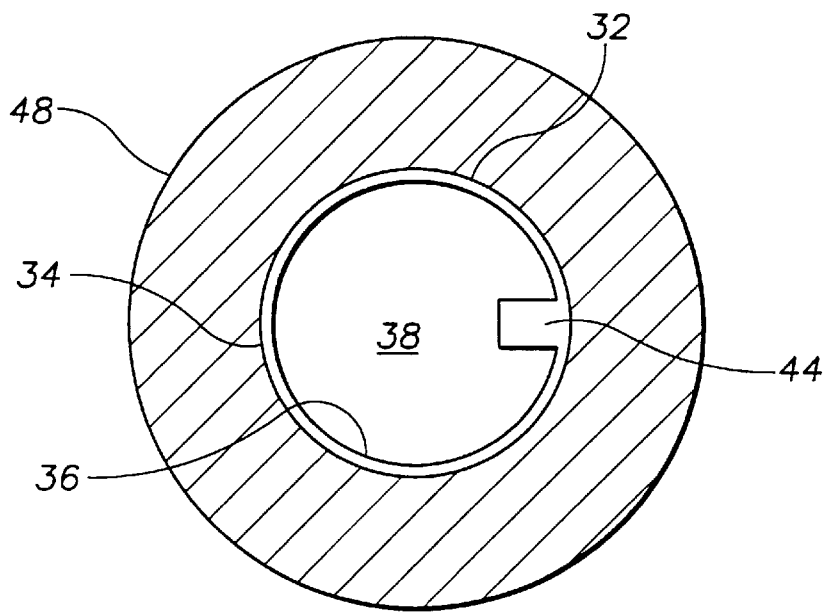
FIG. 4A is a proximal end view of the bone plug removal tool of the present invention illustrating one embodiment of the cutting tooth.
Figure 4B:
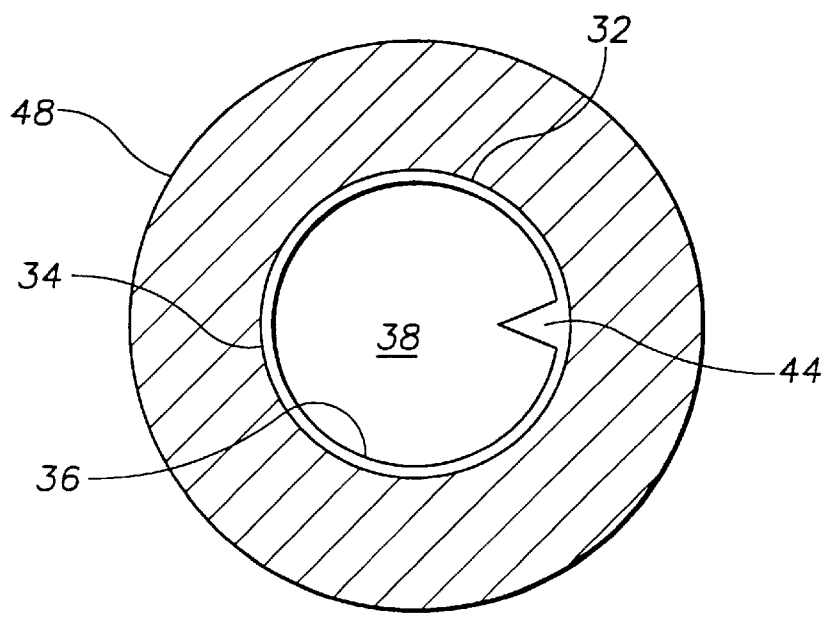
FIG. 4B is a proximal end view of the bone plug removal tool of the present invention illustrating another embodiment of the cutting tooth.

At least one cutting tooth 44 is engaged with the internal surface 36 of the cylindrical cutting element 32 at the proximal cutting edge 42. This tooth 44 extends into the internal bore 38 in a direction that is substantially orthogonal to longitudinal axis 40 of the cylindrical cutting element 32. The cutting tooth 44 is defined by orthogonally extending tooth surfaces 46 that are disposed in parallel. Although a plurality of such teeth may be orthogonally disposed at the proximal cutting edge 42, in the most preferred embodiments of the present invention, only a single cutting tooth is necessary. As shown in FIG. 4A, the cutting tooth 44 is preferably rectangular or square in shape. It is also understood, however, the cutting tooth 44 may be generally triangular in shape as shown in FIG. 4B. The cutting tooth 44, moreover, preferably extends one-fifth of the diameter of the bore 38, although it may range from approximately 1/16 to 1/4 of the bore 38. When the bone plug removal tool 30 is rotated after insertion (to be described in more detail below), the core bone is forced to break loose from the surrounding bone at the cutting edge 42 and the cutting tooth 44 is embedded into the bone. When the tool 30 is extracted, the bone plug is extracted with it. The cutting tooth 44 will also cut a groove along the length of the bone plug which provides additional bone strength when the bone plug is emplaced into a bone hole, as discussed more fully below.

Referring again to FIGS. 2 and 3, the outer cylindrical sheath 48 is arranged concentrically around the external surface 34 of the cylindrical cutting element 32. The sheath has an internal surface 50 that also defines an internal bore 51 extending along longitudinal axis 52 of the sheath 48. In the embodiment illustrated, the outer cylindrical sheath 48 is removably engaged with the cylindrical cutting element 32 by way of matching screw threads 56, 58 located on the internal surface 50 of the cylindrical sheath 48 and on the external surface 34 of cylindrical cutting element 32, respectively. Therefore, the outer cylindrical sheath 48 is removable and may be replaced by another outer sheath having different dimensions by mating the corresponding screw threads. It is particularly preferred that outer cylindrical sheath 48, when engaged with the cylindrical cutting element 32, have a proximal terminus 54 that is not co-extensive with the proximal cutting edge 42 of the cutting element 32. Specifically, the proximal terminus 54 of outer cylindrical sheath 48 is spaced apart from the proximal cutting edge 42 by a distance that defines a depth stop distance X. The depth stop distance X defines the length of the bone plug that is to be removed.

As shown in FIG. 2, an elongated, preferably cylindrical handle 60 may cooperate with the adjacent distal end 43 of the cutting element 32 by way of a second bore 62 that extends through the cutting element 32 orthogonally to the longitudinal axis 40 of the cylindrical cutting element 32. Handle 60 may be inserted after the tool has been driven to the desired depth and is used for rotating the tool to cause the bone to break at proximal cutting edge 42.

It will be appreciated that various other embodiments are intended to be encompassed by the present bone plug tool. For example, handle 60 may be replaced by a conventional screw head (not shown) having a slot defined in it for receiving a screw driver or other, similar device. Handle 60 may also be replaced by a conventional hexagonal nut (not shown) which designed to receive a conventional socket wrench, socket driver or attached drill head. Moreover, although the cutting element 32 is preferably driven into the bone without any rotational movement, such as by hammering or tapping, it is also understood that the cutting element 32 may be screwed or twisted into the bone by means of a screwdriver, socket wrench or other similar device (not shown). In addition, corresponding threads 56, 58 may be replaced in other embodiments by conventional spring loaded snap-fit linkages (not shown). The exact nature of the handle and the nature of the removable coupling between the cylindrical cutting element and the outer cylindrical sheath is not intended to limit the scope of the invention in any way.

The dimensions of the plug removal tool 30 may vary according to the surgical procedures. In preferred embodiments, however, the bone plug removal tool 30 is about 6 inches (152.4 mm) in overall length. If a handle is used, the handle 60 is about 4 inches (101.6 mm) in total length with a diameter of about 0.31 inches (7.9 mm). The outer cylindrical sheath 48 has an outside diameter of 0.30 inch (7.6 mm) to provide sufficient surface area to effectively limit the depth of penetration of the internal cylindrical cutting element 32. The distance between the respective proximal ends of the cylindrical sheath 48 and the cylindrical cutting element 32 will of necessity vary according to the depth of the bone plug. It is contemplated that this distance will vary between 5 mm and 15 mm.

The outside diameter of the cylindrical cutting element 32 at the proximal cutting edge 42 may also vary but is most preferably about 0.25 inches (6.3 mm) with a bore of about 0.196 inches (4.9 mm) inside diameter. Although the bore will preferably range between 4.5 mm and 10 mm, it will again be appreciated that this inside diameter can be smaller or larger depending upon the circumstances.

Figure 5:
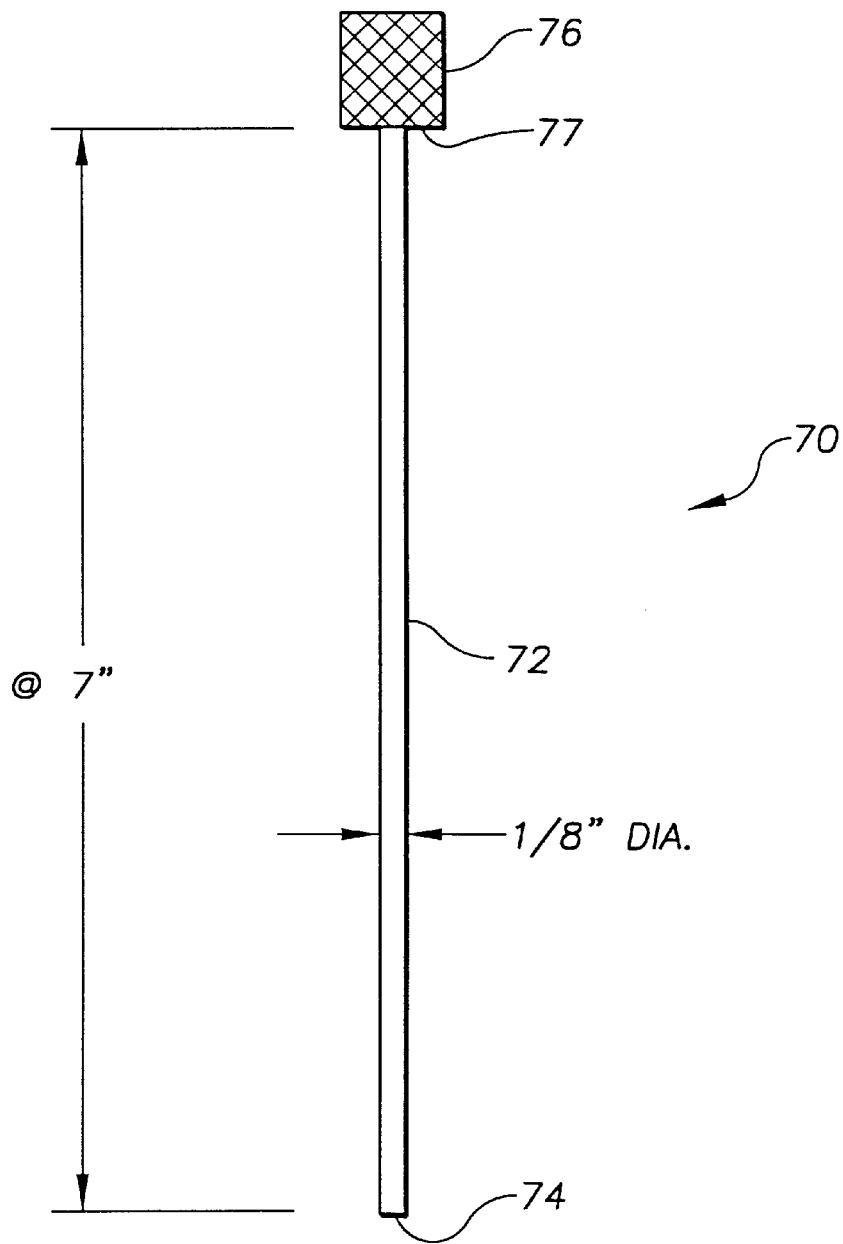
FIG. 5 is a side elevation view of a plunger of the present invention that is designed to remove a bone plug from within the bone plug removal tool.

As discussed above, the bone plug can move freely through internal bore 38 and pass out from the distal end 43 of cutting element 32 after the plug removal procedure has been completed. FIG. 5 illustrates a plunger 70 that is designed to accomplish this. Plunger 70 includes a shaft 72 having a proximal end 74 and a distal portion 76 whose outside diameter is significantly larger than the outside diameter of the rest of the shaft. The differences in outside diameter between the shaft 72 and the distal portion 76 form a step 77 at the junction of the distal portion 76 and shaft 72. The outside diameter of the shaft is sufficiently small so that shaft 72 can be passed between the cutting tooth 44 and the opposite, internal surface 36 of the cylindrical cutting element 32. An exemplary plunger that may be used with the bone plug removal tool has a shaft of about 0.125 inches (3.17 mm) in diameter and at length of about 7 inches (177.8 mm) between its proximal end 74 and the step 77.

Figure 6:
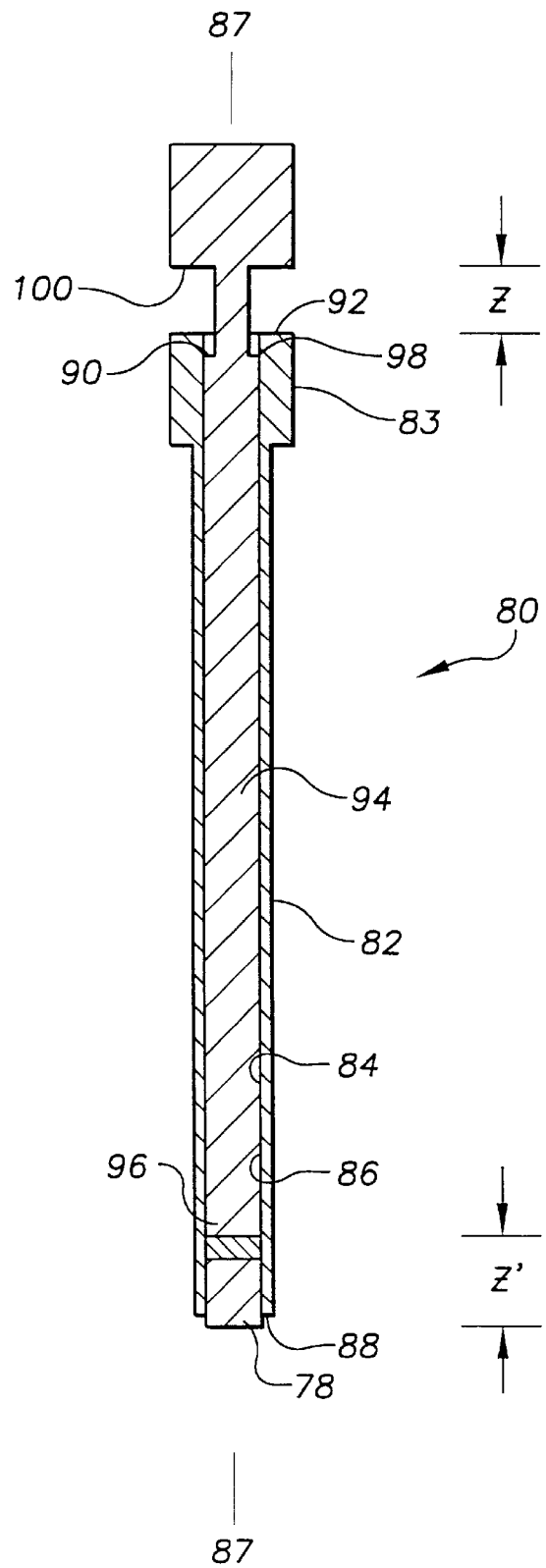
FIG. 6 is a cross sectional view of a bone plug emplacement tool in its distal position.
Figure 7:
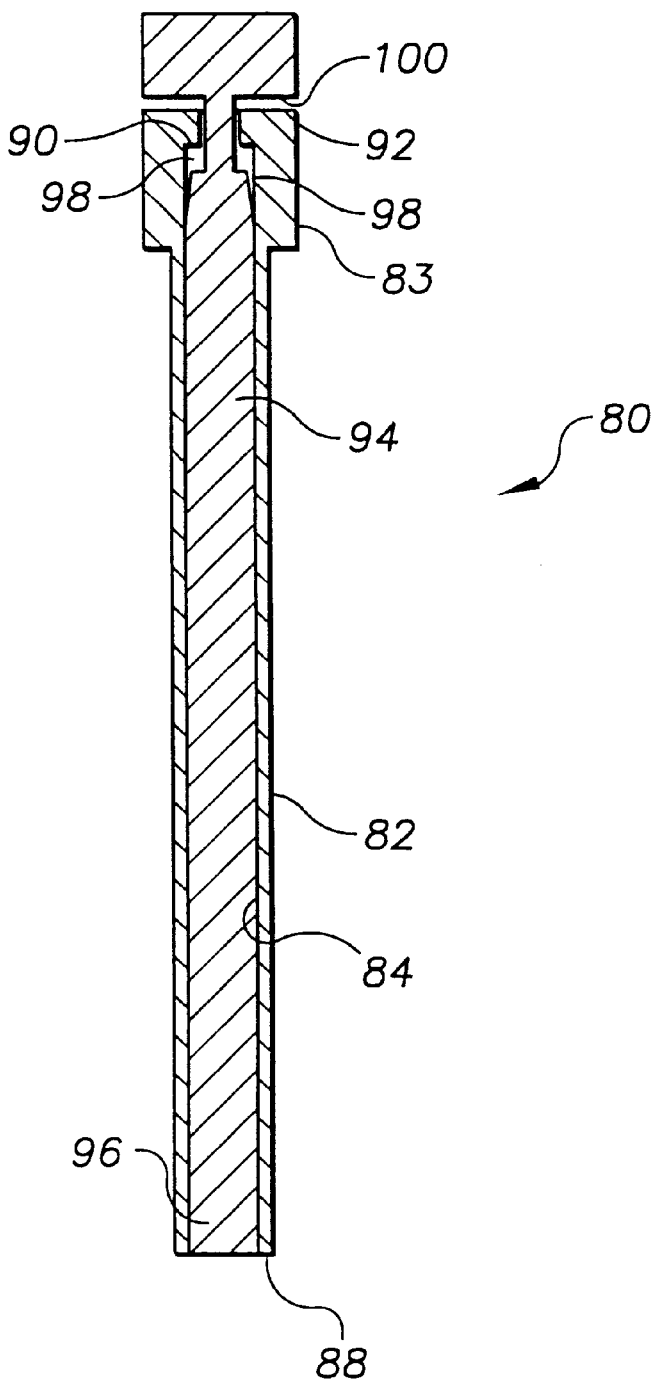
FIG. 7 is a cross sectional view of the bone plug emplacement tool of FIG. 6 in its proximal position.

FIGS. 6 and 7 illustrate a bone plug emplacement tool 80 used to drive an excised bone plug into a drilled bone hole so that defective articular cartilage may be repaired. FIG. 6 also shows a bone plug 78 in place within the emplacement tool 80. Bone plug emplacement tool 80 includes cylindrical element 82 having an internal surface 84 defining an internal bore 86. Element 82 has an expanded section 83 adjacent distal end 92. The internal bore 86 extends along a longitudinal axis 87 of the element 82 from a proximal end 88 of the element 82. Element 82 has a distal end 92. The internal surface 84 further defines, adjacent the distal end 92 of the element 82, an internal step 90.

A stem 94, which may be solid, is disposed within the internal bore 86 and is adapted for co-axial (i.e. distal-proximal) movement. Stem 94 does not have an uniform outside diameter but includes a first shoulder 98 that is designed to mate in facing relationship to the internal step 90 of the cylindrical element 82. When first shoulder 98 and internal step 90 are thus engaged, distal movement of the stem within the internal bore is halted. In this position (FIG. 6), the proximal end 96 of stem 94 is located within internal bore 86 and is spaced apart from the proximal end 88 of the cylindrical element 80. The respective proximal ends 88, 96, define between them an internal bone plug receiving space that is configured to receive the bone plug 78 that is to be emplaced. In the embodiment illustrated, the stem 94 extends distally from the distal end 92 of cylindrical element 82.

At some distance from distal end 92, the stem 94 has defined in it a second shoulder 100. The second shoulder 100 is designed to engage with the distal end 92 of element 82 and this engagement limits the proximal movement of the stem 94 within the internal bore 86. The distance (Z) between the second shoulder 100 and distal end 92 of the cylindrical element 82 is designed to be at least equal to the longest dimension of the bone plug 78. Similarly, the distance (Z') between the proximal end 96 of stem 94 and the proximal end 88 of the cylindrical element 82 is also at least equal to the longest dimension of the bone plug 78 and equal in length to the length of the internal bone plug receiving space. Proximal movement of the stem 94 within the internal bore 86 of the emplacement tool 80 will completely disgorge the bone plug 78 into a drilled bone hole. In preferred embodiments, the distance (Z) between the second shoulder 100 and the distal end 92 of the cylindrical element 82 is slightly less than the bone plug depth. For instance, in a 5 mm long bone plug, Z is 4 mm; for a 10 mm long bone plug, distance Z is 9 mm; for a 15 mm bone plug, distance Z is 14 mm, and so on. Thus, the distance (Z') between the proximal end 96 of the stem 94 and the proximal end 88 of the cylindrical element 82 is also slightly less than the bone plug depth. Specifically, if the bone plug is 5 millimeters long, the distance (Z') between the respective proximal ends 88, 96 is 4 millimeters so that one millimeter of bone will protrude from the proximal end 88 of the cylindrical element 82. This protruding section assists the operator in finding the drilled bone hole prior to emplacement.

The stem 94 is adapted for movement from a distal position (FIG. 6), where the first shoulder 98 and the internal step 90 are engaged and the respective proximal ends 88, 96 define between them the internal bone plug receiving space. The stem 94 then moves to a proximal position (FIG. 7) where the second shoulder 100 engages with the distal end 92 of cylindrical element 82 and the bone plug is disgorged from within the internal bone plug receiving space, as described below. An exemplary emplacement tool that is compatible with the bone plug removal tool discussed previously has a cylindrical element that defines an internal bore of about 0.196 inches (4.9 mm) inside diameter. The outside diameter of the cylindrical element may be about 0.25 inches (6.3 mm) in diameter. The length of the cylindrical element from its proximal end to the beginning of the expanded section 83 may be about 5.5 inches (139.7 mm) in length.

The surgical technique described herein is preferably performed arthroscopically using conventional equipment, although open techniques may be utilized should proper bone plug insertion prove impossible by arthroscopic means. Before surgery, a bone plug removal tool of the present invention is prepared. A standard anterolateral or medial or superior portal is used to introduce a 4.5 mm, 30° oblique arthroscope, and a shaver is applied through an anteromedial portal to prepare the articular cartilage defect. After shaving the degenerated cartilage in the vicinity of the defect, an 8 mm skin incision is made on the superolateral corner of the patellofemoral joint. The bone plug removal tool 30 is inserted through this portal and at least one cylindrical bone plug (5 mm in diameter and 10 mm in length) is taken from the lateral wall of the patellar groove, located outside the patellofemoral joint. A bone plug may also be taken from the anterolateral side of the intercondylar area. Three holes, each with a diameter of 4.8 mm, are then made using a drill bit through the anteromedial portal. The bone plug is removed from the removal tool 30 using the plunger 70 and positioned within the emplacement tool 80, as described below. The bone plug emplacement tool 80 of the invention containing the bone plug in its correct orientation is placed over the hole through this portal and the bone plug is pushed into the hole using the emplacement tool 80, as described herein.

Figure 8A:
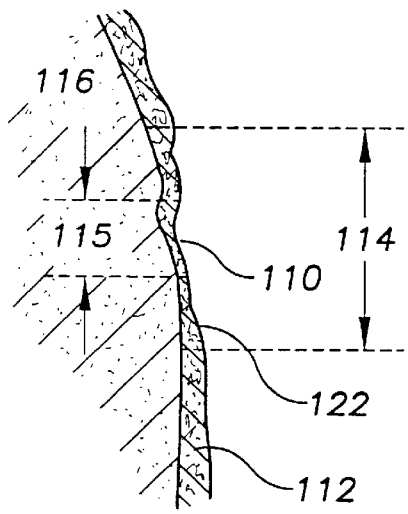
FIGS. 8A through 8D are cross-sectional views of a fragment of bone through section 8—8 of FIG. 1 illustrating the orientation of the bone hole and bone plug of the present surgical technique.
Figure 8B:
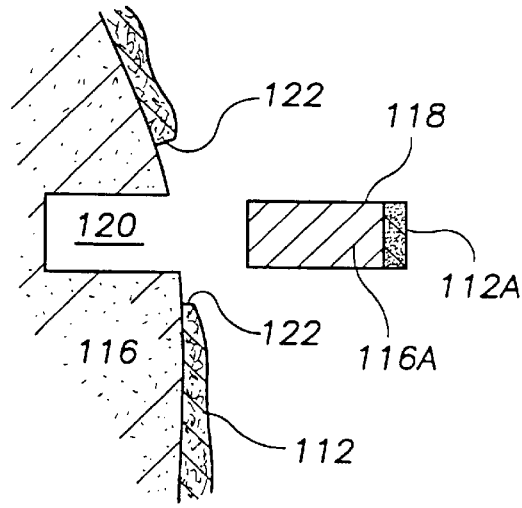
Figure 8C:
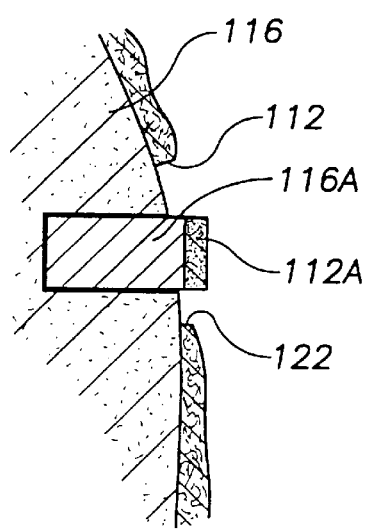
Figure 8D:
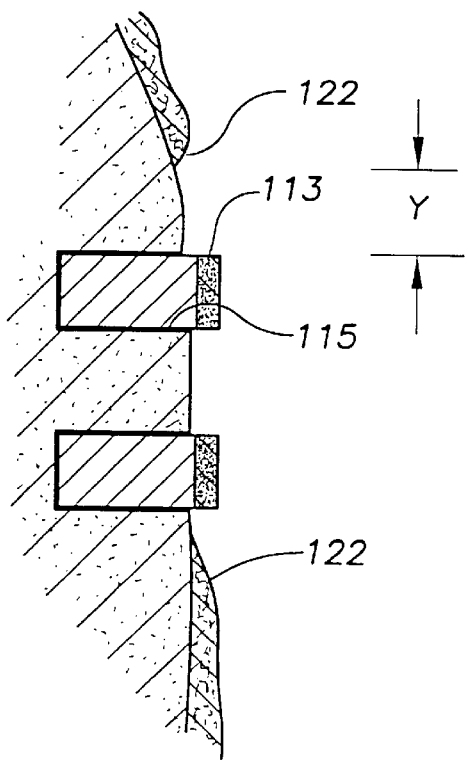

Referring generally to FIGS. 8A–8D, the present invention contemplates repairing a defect or damaged area 110 in an articular cartilage 112 by removing a conveniently shaped (for example circular) portion 114 of the defective articular cartilage layer 112 and a portion 15 115 of the underlying bone 116. FIG. 8A illustrates the general principle, discussed more fully below, that the surface area of the bone portion removed 115 is not necessarily coextensive with the surface area 114 of cartilage removed. The edges 122 of the defect 110 are debrided to create vertical walls and sharp edges. The base of the defect is shaved smooth but is not abraded through to the subchondral bone. The size of the removed portion 114 is kept to a minimum but is large enough to include the whole of the damaged cartilage area.

The bone is drilled with a hand or power drill containing a drill bit that most preferably has an expanded outside diameter (i.e., a depth stop countersink) located some distance distal to the proximal end of the drill bit. An exemplary drill bit used with the present methodology has a cutting surface exactly equal to the chosen length of the bone plug. That is, the cutting surface can be between about 5 mm and 15 mm in length. The outside diameter of such an exemplary drill bit is very slightly undersized relative to the inside bore diameter of the bone core removal tool. In particular, an internal bore of 0.196 (4.97 mm) inside diameter for the cylindrical cutting element of a bone core removal tool would require a drill bit of 0.190 (4.82 mm) inches outside diameter. The difference of 0.006 (0.15 mm) inches is necessary for the required interference fit of the bone plug within the drilled bone hole. The outside diameter of the drill bit begins its expanded depth stop section at a distance above the proximal end that is equal to the depth of the bone plug. This expanded section may be 0.25 inches (6.35 mm) in diameter and can be about 6 inches (152.4 mm) long.

Bone holes drilled into the underlying bone may be of any depth but are most preferably about 5 mm to about 15 mm in depth. It is most preferred that excised plugs of articular cartilage with the underlying subchondral cancellous bone attached have a total length of about 10 mm. This will provide individual bone plugs having about 5 mm of cartilage and 5 mm of bone or other similar combinations such as 2 mm of cartilage and 8 mm of bone, 3 mm of cartilage and 7 mm of bone, etc.

Figure 9:
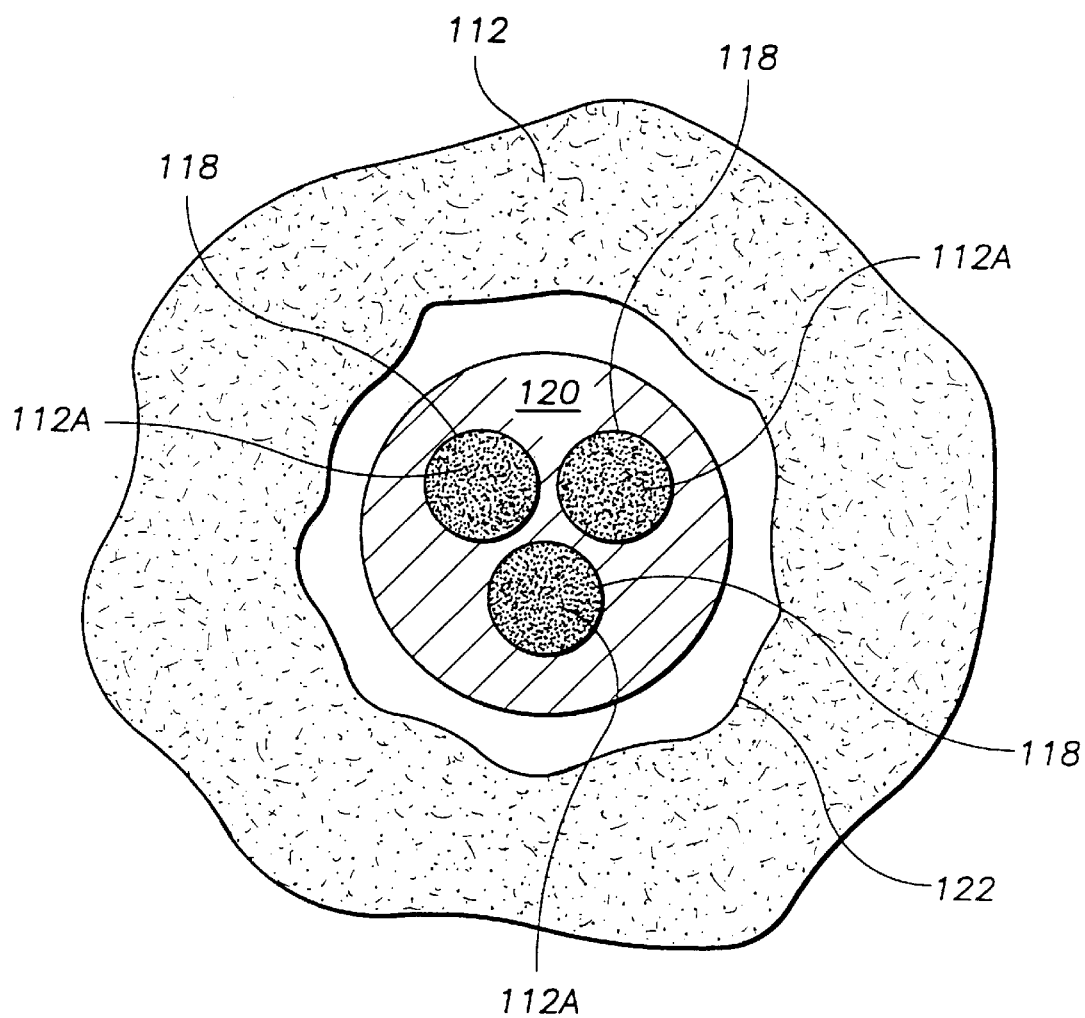
FIG. 9 is a front elevation view of a plurality of bone plugs received within a single drilled bone hole within an articular cartilage defect.

Depending on the size of the defect and of the underlying bone hole, several bone holes may be drilled, each bone hole designed to receive a single bone plug (FIG. 8D) or a single bone hole may be drilled to receive a plurality of bone plugs (FIG. 9).

Following removal of the articular cartilage portion of the damaged area 110, as well as the underlying bone, a correspondingly sized and shaped bone plug 118 is inserted, first into and through the opening 114 left in the articular cartilage layer 112, and then into the underlying drilled bone hole 120. The bone plug 118 contains both bone 116A and its overlying articular cartilage 112A. These plugs will most preferably be taken from the non weight-bearing surfaces of the joint principally in the intracondylar notch and the periphery of the condyle. The bone plug 118 is inserted into the drilled bone hole 120 so that the articular cartilage layer 112A of bone plug 118 is in lateral registration with (i.e., is aligned with) the articular cartilage layer 112 surrounding the drilled bone hole 120.

The bone plug 118 is of sufficient shape to maintain a frictional fit within the drilled bone hole 120 and will remain there until such time as tissue ingrowth from the surface of the bone and peripheral, cut edges 122 of the articular cartilage layer 112 surrounding the bone hole 120 more permanently fix the bone plug 118 in place.

Bone plugs 118 may be positioned within a single bone hole 120 so that their respective outer peripheral edges are not in contact with each other. More preferably, individual bone plugs 118 located in their respective bone holes 120 may have their centers between 3 mm and 5 mm apart (See FIG. 8D). The peripheral edges 113, 115 of a given bone plug 118 are preferably positioned at some distance (Y) from the cut edges 122 of the defect and it is preferred that this distance be no further than about 5 mm.

These rules for bone plug spacing and orientation allow for a variety of possible configurations. For example, an articular cartilage defect 10 mm in diameter may accommodate one 5 mm diameter plug in the center of the defect. A defect 20 mm in diameter may be divided into four, 10 mm diameter quadrants and four holes drilled in the underlying bone. The defect therefore receives a total of four bone plugs.

Although the bone plug 118 is designed to have a friction fit into the drilled bone hole 120, several temporary fixation techniques are available. One such technique involves sewing sutures through the respective peripheral edges 113 of the articular cartilage layer 112A adhering to the bone plug and the articular cartilage 122 of the surrounding tissue. Alternatively, an adhesive layer (not shown) may be provided between the bone plug 118 and drilled bone hole 120. This adhesive layer allows time for sufficient ingrowth of tissue from the surrounding environment so that bone plug is locked into place in the bone hole. Various bio-adhesives are well known in the art. See for example U.S. Pat. No. 5,067,964 (fibrinogen and thrombin sealant). Bone growth or cartilage growth promoting chemical factors may also be added. These may include cartilage-derived growth factor (CDGF—See U.S. Pat. No. 5,376,636), various inteleukins, colony-stimulating factor (CSF), osteopontin, platelet-derived growth factor (PDGF) and bone morphogenic protein (BMP-1). See also U.S. Pat. No. 5,373,503, incorporated herein by reference.

In use, the bone plug removal tool 30 is positioned above the bone/cartilage surface and the proximal cutting edge 40 of the cylindrical cutting element is preferably tapped with a hammer (not shown) to seat the proximal cutting edge 40. When the tool 30 is fully seated in the bone, the handle 60 is turned a minimum of 360° degrees and the cylindrical cutting element 32 engages the bone down to a depth that is limited by contact of the proximal terminus of the outer sheath 54 with the bone surface. The outer sheath 54 does not cut into the bone. The tool 30 is then pulled distally away from the bone with a twisting action to remove the bone plug. The plunger 70 is then inserted through the proximal cutting edge 42 of the bone plug removal tool 30 to push or tap the bone plug through the internal bore 38 and out the distal end 43 of the bone plug removal tool 30. The excised bone plug is then manually inserted, typically by the surgeon, into the receiving space of the emplacement tool 80, articular cartilage surface 112A first. This insures proper orientation of the bone plug within the receiving space so that the excised articular cartilage layer 112A is engaged with the proximal end of the stem 96. It is particularly preferred that about one millimeter (1 mm) of underlying bone protrude from the proximal end 88 of the cylindrical element 82. This configuration allows the operator to find the drilled bone hole more easily. Once located, the bone plug is pressed into the drilled bone hole by moving the stem 94 from the distal to the proximal position so that the excised bone plug can be disgorged into the bone hole. The holes drilled in the donor defects are filled with collagen plugs.

Post operative rehabilitation may include nonweight bearing for eight weeks with crutches. Full active motion of the knee will be encouraged such as "nonweight bearing" exercise with a stationary bike using minimal resistance but high speed. This is useful for thigh rehabilitation as soon as pain and swelling permits. Running and pivoting activities should not be allowed until after healing is confirmed either radiographically or by relook arthroscopy.

An exemplary prospective study to assess the effectiveness of this technique is now described. Patients are selected with significant full thickness articular cartilage defects located on the weight bearing surface of the femur. To be included in the study, patients are a minimum age of 14 years, have a thickness defect in the distal femoral condyle that includes those caused by osteochondritis dissecans and trauma that is at least 10 mm but no larger than 30 mm in diameter, adequate bone density, a willingness to comply with the study protocol, and a commitment to return for at least two years follow up. No patient with an active infection, who does not meet all of the inclusion criteria, or who has had prior knee surgery that would compromise the vascular supply is included.

Preoperative assessment includes a history including any identifiable etiology of the defect, a physical and radiographic evaluation, and the completion of both the Lysholm knee scoring scale and Tegner activity level scale. The objective evaluation includes tests for mensical signs, range of motion, atrophy, effusion, instability (Lachman, anterior drawer, and pivot shift), and patellofemoral problems. Baseline radiographs are obtained. The findings at surgery and procedures performed are recorded.

Post operative assessments occur at intervals of 1, 2, 3, 6, 12, and 24 months. These assessments are essentially the same as the preoperative evaluations and include the data for the Lysholm and Tegner scale and knee radiographs.

Additional Embodiments

FIGS. 10–14 illustrate a bone plug removal and emplacement tool according to a further embodiment of the invention. In this embodiment, a harvesting tube is disposed within the cutting element to facilitate removal and emplacement of a plug cut from the bone. That tube, which receives the plug as it is cut, can be slidably withdrawn from the cutting element and evacuated by a plunger that forces the plug, into a recipient bone hole.

Cutting Element

Figure 10:
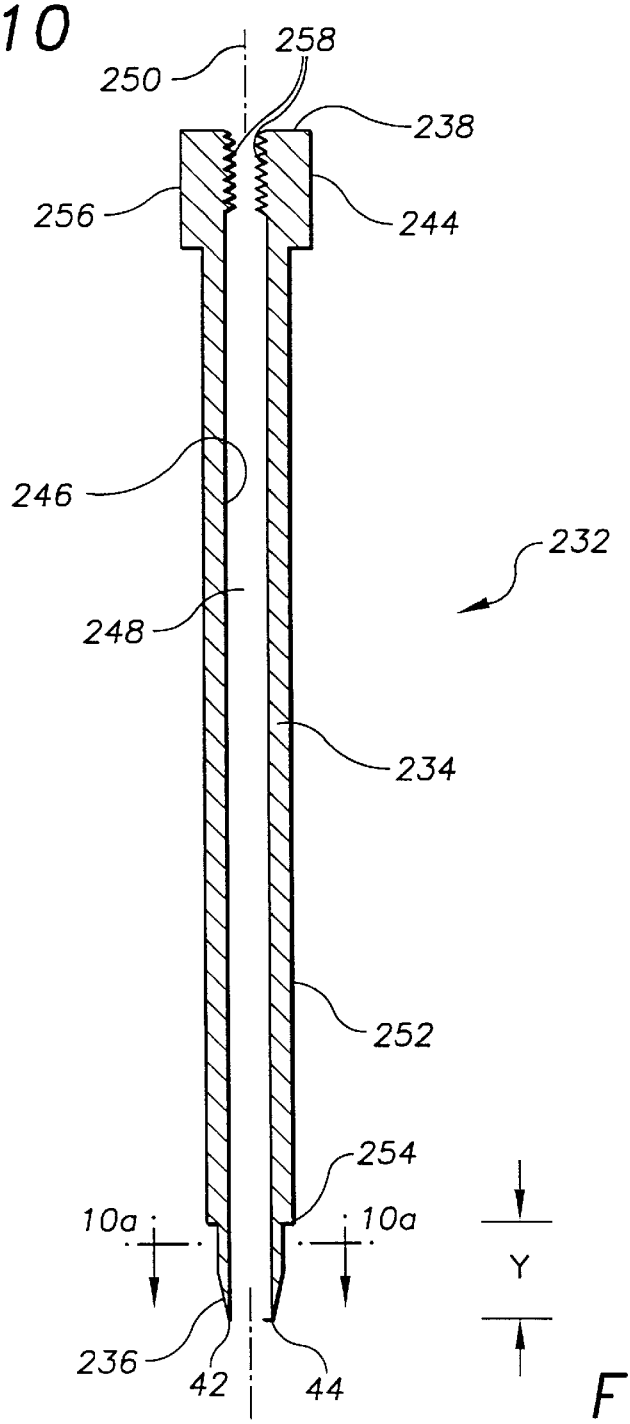
FIGS. 10–10A are cross sectional views of the cutting element of a bone plug removal and emplacement tool according to the invention.
Figure 10A:
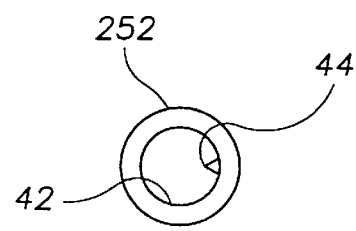

With particular reference to FIG. 10, there is shown a cannulated cylindrical cutting element 232 used in connection with the bone plug removal and emplacement tool, particularly, for bone plug removal and harvesting. The element 232 is configured substantially like the cutting element 32 of FIGS. 2, 3 and 4, except insofar as its distal end includes a collar and internal threading, rather than a handle and external threading, and except insofar as described below. The body 234 of cutting element 232 is generally cylindrical in shape, though, conical and other shapes may be employed as well. At the proximal end 236 of element 232 are cutting edge 42 and one or more teeth 44, which are constructed and utilized as described in the embodiments above. A cross-sectional view of the distal end of element 232 is provided in FIG. 10A.

The cutting element 232 is dimensioned in accord with type of surgery with which it will be used, as well as the size of the bone plug to be removed. In a typical configuration for arthroscopic knee surgery, the element 232 is machined from surgical stainless steel (or other appropriate material) and is approximately 5 to 10 inches in length and, preferably, around 6 inches in length. The outside diameter of the cylindrical cutting element 232 at the proximal cutting edge 42 may also vary but is most preferably about 0.25 inches (6.3 mm). The bore diameter ranges between 4.5 mm and 10 mm and, preferably, 4.9 mm, depending upon the circumstances of use.

Cutting element 232 can include a removable outer cylindrical sheath that serves as a depth stop in the manner of sheath 48 described above. Alternately, as shown in FIG. 10, the cutting element 232 can include an integral step 234 to define such a depth stop. That step can be machined or molded in the conventional manner. Those skilled in the art will appreciate that other configurations, such as protruding pins, can be employed to serve as depth stops, as well.

Illustrated depth stop 234 has sufficient surface area to stop that portion of the cutting element 232 distal to it from penetrating into the bone. Thus, for example, in an embodiment in which the outer diameter of the cutting element 232 proximal to the step is, e.g., about 0.25 inches (6.3 mm), that distal to the step is, e.g., 0.30 inch (7.6 mm). As with sheath 48, the distance Y between the proximal end of cutting element 232 and step 234 will of necessity vary according to the depth of the desired bone plug, though, typically falls between 5 mm and 15 mm and, preferably, is 8 mm.

A collar 244 disposed at the distal end 238 of the cutting element 232 effects a further step in the outer surface of 252. The collar 244, which too is preferably integral to element 232, provides reinforcement and aids in gripping the cutting element 232. For the latter purpose, the surface of collar 244 is preferably knurled or roughened. Those skilled in the art will appreciate that the collar 244 is optional and, if employed, can utilize other configurations as well.

An internal surface 246, which extends from the proximal end 236 to the distal end 238 of the cutting element 232, defines a bore 248 that runs the length of the cutting element 232 about a longitudinal axis 250. Threads 258 are provided on the internal surface 246 at the distal end of the bore 248. The threads 258 provide a means for locking engagement, e.g., with a harvester as described below.

Harvester

Figure 11:
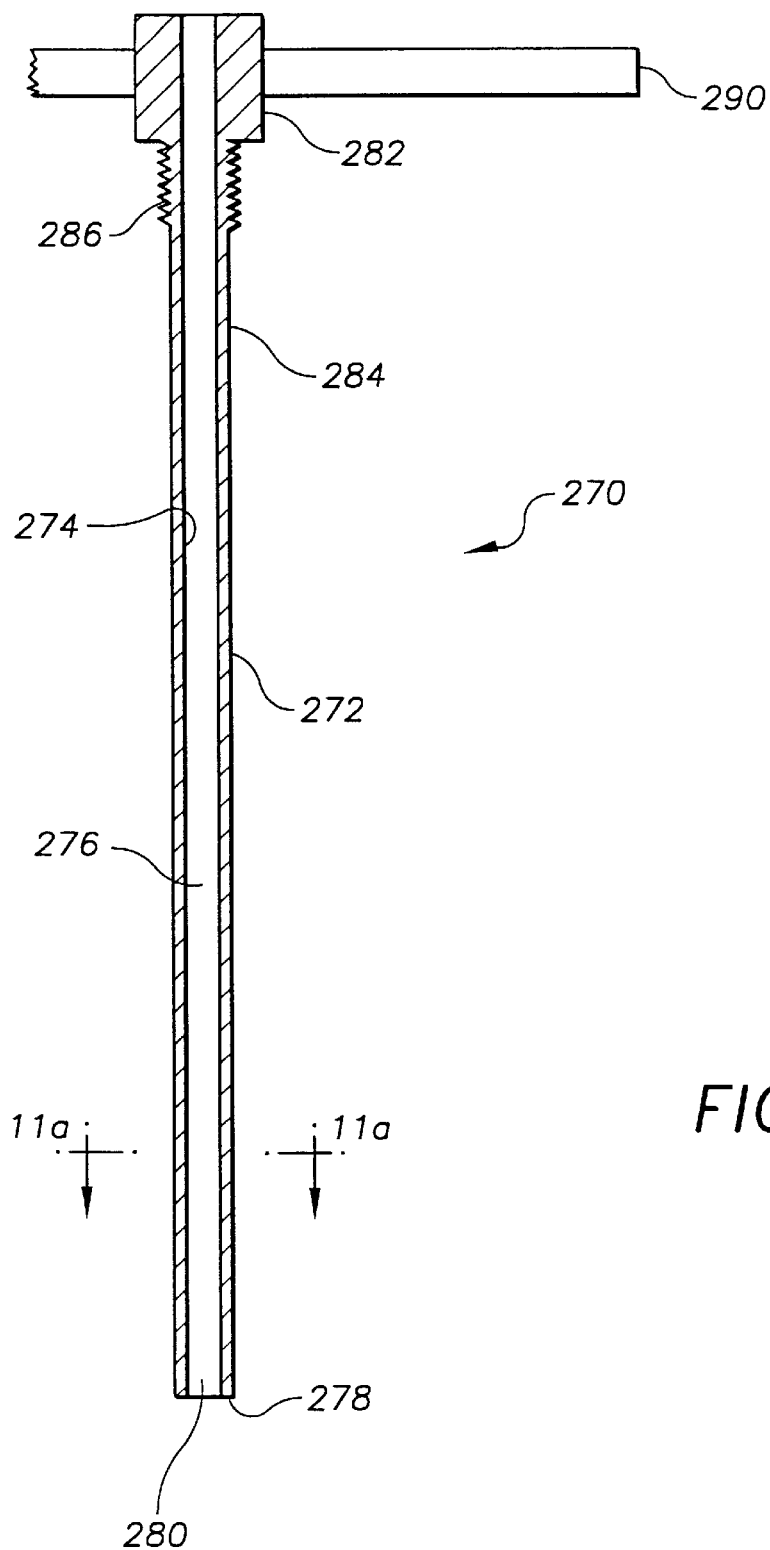
FIGS. 11–11A are cross sectional views of a harvester element of a bone plug removal and emplacement tool according to the invention.
Figure 11A:
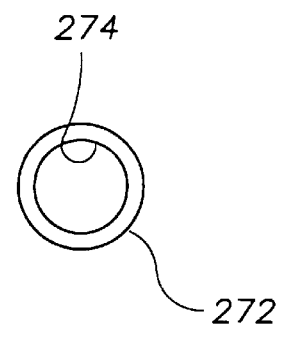

FIG. 11 shows a harvester 270 used in connection with a bone plug removal and emplacement tool according to the invention. A cross-section of the harvester is shown in FIG. 11A. The harvester 270 comprises a cannulated tube 272 that is adapted to be slidably received in the cutting element bore 248. It includes an inner surface 274, defining bore 276 whose distal end comprises a cavity 280 for receiving a bone plug cut by the cutting element 232.

At the distal end of the tube 272 is a collar 282 and, proximal thereto, threads 286 for engagement with the threads 258 of the cutting element 232. Upon mating the harvester threads 286 with the cutting element threads 258, the harvester 270 and cutting element 232 become fixedly engaged for cutting and harvesting a bone plug. Those skilled in the art will appreciate that the threads 258, 286, though preferred, are optional and are not required to maintain the harvester 270 in engagement with the cutting element 232 during plug cutting and harvesting. Thus, for example, the harvester 270 and cutting element 232 can be mated by spring loaded snap-fit linkages, interference fit, etc.

The harvester 270 may also include a handle 290 located at the distal end 280 of the harvester and preferably mounted through the harvester collar 282. As with handle 60, described above, handle 290 may be mounted at different locations on the harvester or on the cutting element 232. The handle 290 provides leverage for turning the cutting element 232 about its longitudinal axis 250. As above, the exact nature of the handle and the nature of the removable coupling between the harvester 270 and the cylindrical cutting element 232 is not intended to limit the scope of the invention in any way.

The harvester 270 is sized in accord with the bone cutting element 232. Thus, tube 272 is of a length such that its proximal ends is substantially aligned with the proximal end of cutting element 232 (with respect to longitudinal axis 250) when the tool 230 is assembled tool. Put another way, in the assembled device, the proximal end of the tube 272 substantially abuts the cutting edge 42 and the distal surface of tooth 44, without interfering with operation of either of them. In alternate embodiments, the proximal end of the tube is set back from that of the cutting element 232. Preferably, that set back is less than 50% and, preferably, less than 10% of the depth stop distance Y, so that harvested bone plugs are adequately protected by the tube 272. The outer diameter of the harvester proximal end 278 is substantially equal to, though slightly smaller (e.g., 1%–15% and, preferably, 5%) than the inner diameter of cutting element bore 248. The wall of tube 272 at the proximal end (or cavity) is 0.1–0.5 mm and, preferably, about 0.3 mm. This is sufficiently thick to protect the bone plug during removal and emplacement, yet not so thick as to cause it to be crushed or deformed during harvesting.

In the illustrated embodiment, bore 276 is of constant diameter from the proximal end 278 to the distal end 280 of the harvester 270. In alternate embodiments, the diameter of the bore 276 distal to the cavity may be smaller than that of cavity 280 itself. As the cavity 280 defines the region in which removed bone plugs reside, the cavity length (along longitudinal axis 250) is preferably substantially equal to or greater than depth stop distance Y.

Bone Plug Removal Configuration and Operation

Figure 12:
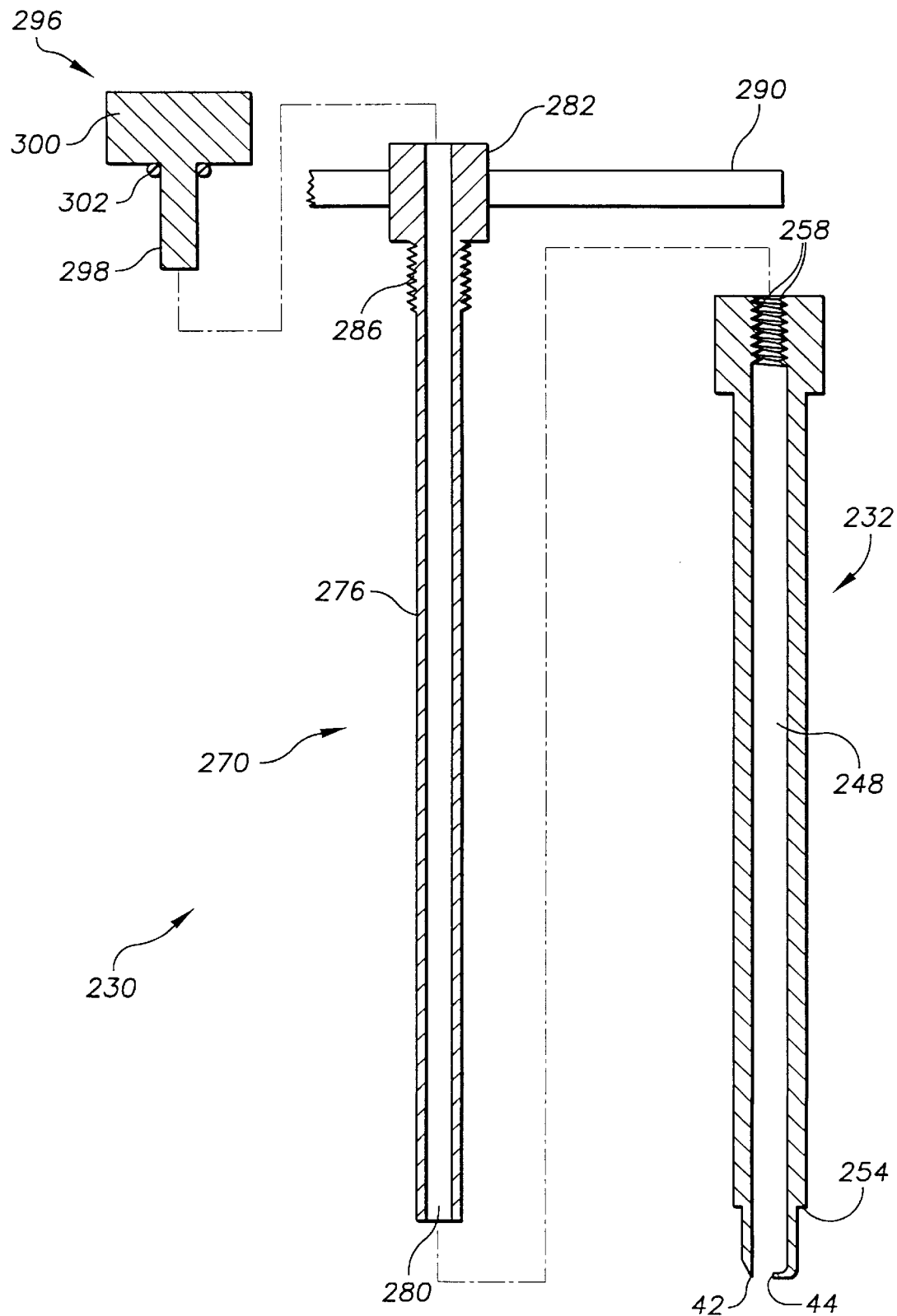
FIG. 12 is an exploded view of a bone plug removal and emplacement tool configured for bone plug removal.

FIG. 12 shows an exploded view of the aforementioned bone plug removal and emplacement tool 230 configured for bone plug removal. The assembled tool is shown in cross-section in FIG. 13. These drawings show that the harvester 270 is inserted in the bore 248 of cutting element 232 and, preferably, maintained there by cooperative action of threads 258, 286.

As above, assembled tool 230 may be driven into the bone in numerous ways, e.g., via screwing or twisting it into the bone by means of a screwdriver, socket wrench or other similar device (not shown). Preferably, however, it is driven into the bone without any rotational movement, such as by hammering or tapping. Transmission of such force from the distal end of the tool 230 is facilitated by illustrated anvil 296 having a stem 298 extending from its body 300. The anvil 296 may comprise metal, rubber, plastic, or other suitable material. The anvil 296 is mounted to the harvester 270 by inserting the stem 298 of the anvil 296 into the distal end of the bore 276 of the harvester 270. Optional o-ring 302, preferably made of rubber or plastic, provides a buffer between the anvil 296 and the harvester 270.

The assembly 230 can be utilized in open or, preferably, arthroscopic surgery to remove and harvest a bone plug, generally as described above. Thus, a skin incision is made and the proximal end of the assembled tool 230 is inserted therethrough. The cutting edge 42 of the cutting element 232 is positioned on the bone surface from which the plug is to be taken, e.g., superior and lateral aspects of the interchondular notch. The edge 42 is preferably positioned perpendicular to the bone surface, e.g., via line-of-sight viewing or via use of the indicator element described in copending commonly assigned U.S. patent application Ser. No. 08/399, 428. Upon tapping the anvil 296, e.g., with a mallet (not shown) or other such object, the proximal ends of the cutting element 232 and harvester 270 are driven, e.g., 8 mm into the bone, until stopped by depth stop 254.

Figure 13:
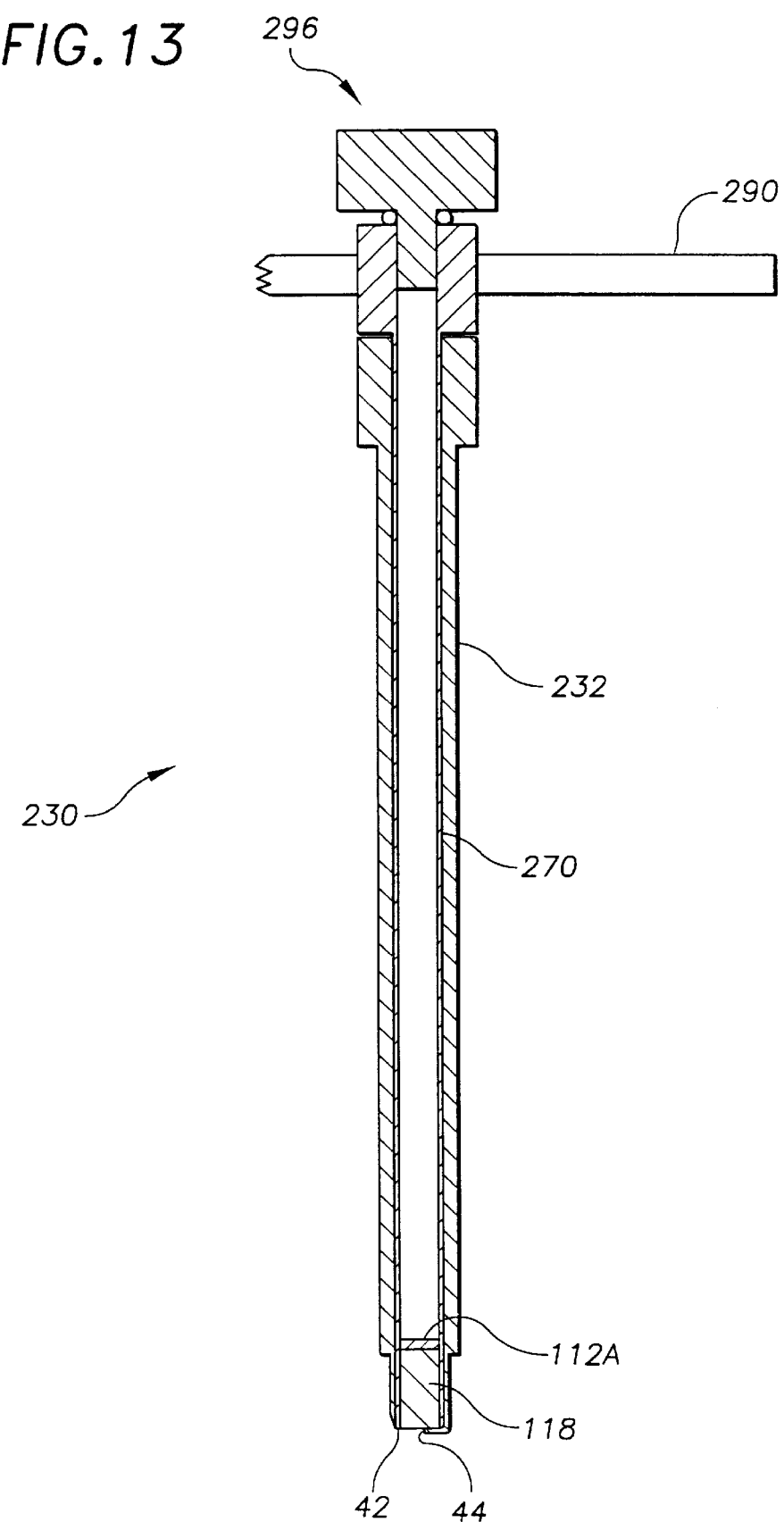
FIG. 13 is a cross sectional view of the tool of FIG. 12.
Figure 14:
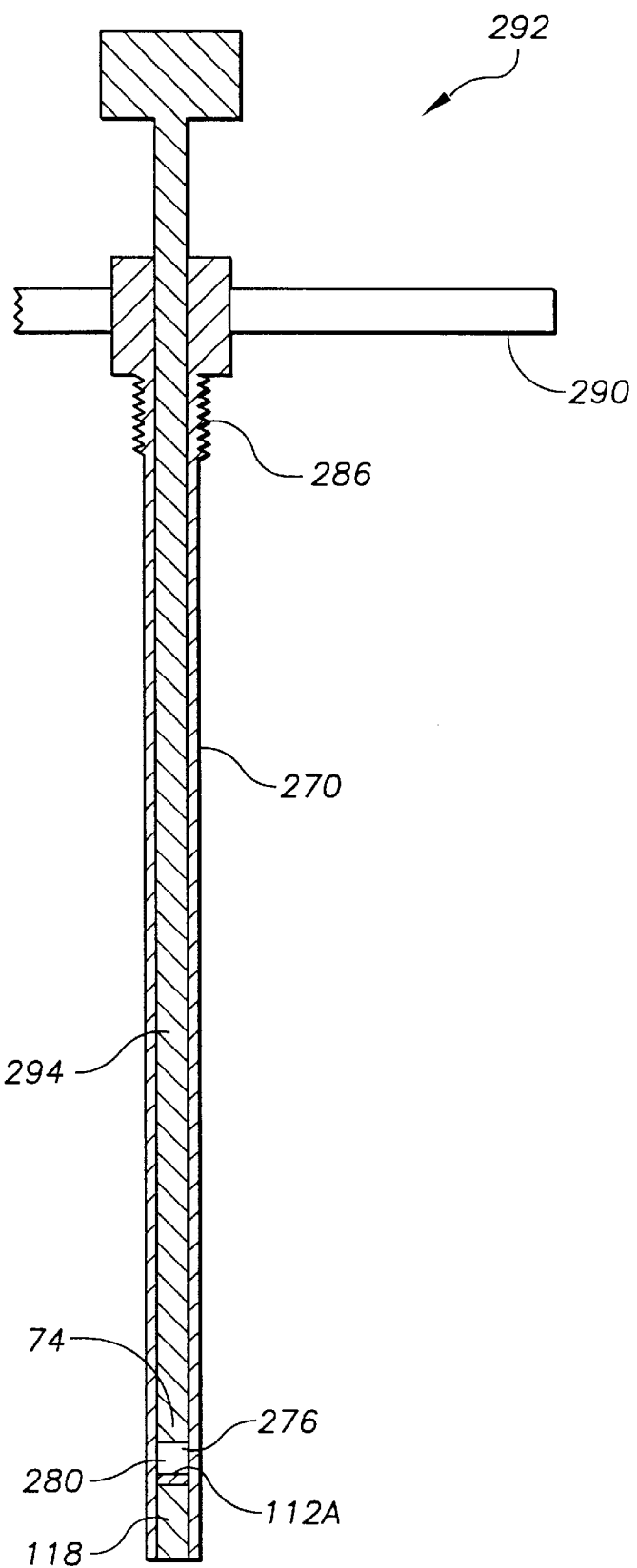
FIG. 14 is a cross sectional view of a bone plug removal and emplacement tool configured for bone plug emplacement.

Once its proximal end is inserted into the bone, the tool 230 is rotated as described above, e.g., via handle 290, so that tooth 44 undercuts the bone plug, forcing it to break loose from the surrounding bone. FIG. 13 shows such a bone plug 118 and its overlying articular cartilage 112A contained within harvester cavity 280 of the assembled tool 230.

Bone Emplacement Configuration and Operation

After a bone plug is harvested, the harvester 270 is separated from the cutting element 232, e.g., by unscrewing the harvester and slidably removing it. The bone plug 118 with articular cartilage 112A remains protected in the cavity 280 at the proximal end of the harvester until it is ready for transplant into the recipient bone hole. If additional bone plugs are required, additional harvesters 270 can be assembled to the cutting element 232 and the foregoing process repeated.

Harvester 270 containing bone plug 118 (with cartilage 112A) is positioned over a recipient bone hole 120, which is created and prepared as discussed above. This can be facilitated by, first, screwing the harvester 270 into an optional endoscopic delivery guide (not shown) configured, dimensioned and constructed like cutting element 232, but without cutting edge 42 and tooth 44. After the harvester 270 is positioned, a removable plunger 292 is inserted into bore 276 in pushed in the proximal direction to disgorge bone plug 118 into the bone hole 120.

Plunger 292 is constructed substantially like plunger 70, described earlier, sans shoulder 98. Particularly, shaft 294 of plunger 292 has an outer diameter between 25% and 99% and, preferably, between 80% and 90% of the inner diameter bore 276. Shaft 294 also has a length sufficient to push the bone plug 118 out of cavity 80 and, preferably, about 1–5 mm further into bone hole 120.

A further appreciation of the construction and operation of the embodiment shown in FIGS. 10–14 may be attained by reference to the schematics and other materials provided in the Appendices filed herewith.

Conclusion

It should be understood that the preceding is merely a detailed description of certain preferred embodiments. It therefore should be apparent to those skilled in the art that various modifications and equivalents can be made without departing from the spirit or scope of the invention.

What is claimed is:

1. A surgical assembly comprising a bone plug removal tool including:
   a cylindrical cutting element having an internal surface defining an internal bore extending along a longitudinal axis of the cutting element from a proximal end;
   a first cutting edge located at the proximal end of the cutting element for cutting a plug of bone as the cutting element is driven into a bone;
   at least one cutting tooth located substantially at the proximal end of the cutting element and extending into the internal bore of the cutting element in a direction that is substantially orthogonal to the longitudinal axis of the cylindrical cutting element; and
   the cutting tooth being defined by at least two planar and parallel surfaces extending substantially orthogonal to the longitudinal axis of the cutting element so as to form a second cutting edge for undercutting the bone plug when the first cutting edge is rotated inside the bone.

2. A surgical assembly according to claim 1, wherein the cutting element comprises a plurality of cutting teeth substantially at the proximal end of the cutting element.

3. A surgical assembly according to claim 1, wherein the cutting tooth is any of substantially rectangular and substantially square in shape.

4. A surgical assembly according to claim 1, the cutting tooth is substantially triangular in shape.

5. A surgical assembly according to any of claims 3 and 4, wherein the cutting tooth extends between $\frac{1}{16}$ and $\frac{1}{4}$ of a diameter of the internal bore of the cutting element.

6. A surgical assembly according to claim 5, wherein the cutting tooth extends one-fifth of the diameter of the diameter of the internal bore.

7. A surgical assembly comprising a bone plug removal tool including:
   a a cylindrical cutting element having an internal surface defining an internal bore extending along a longitudinal axis of the cutting element from a proximal end to a distal end of the cutting element,
   a cutting edge located at the proximal end of the cutting element for cutting a plug of bone as the cutting element is driven into a bone,
   at least one cutting tooth located substantially at the proximal end of the cutting element and extending into the internal bore of the cutting element in a direction that is substantially orthogonal to the longitudinal axis of the cylindrical cutting element, and
   a harvester disposed within the internal bore of the cutting element, the harvester having a proximal end with an internal surface defining a cavity for receiving the plug of bone cut by the cutting edge.

8. A surgical assembly according to claim 7, wherein the havester is removably disposed within the cutting element.

9. A surgical assembly according to claim 7, wherein the havester is slidably disposed within the cutting element.

10. A surgical assembly according to claim 7, wherein the cavity of the harvester has a proximal end that is substantially aligned with the proximal end of the cutting element.

11. A surgical assembly according to claim 10, wherein the proximal end of the cavity is substantially aligned with the cutting edge of the cutting element.

12. A surgical assembly according to claim 10, wherein the proximal end of the cavity is substantially aligned with the proximal end of the tooth of the cutting element.

13. The assembly of claim 7, wherein the inner surface of the harvester comprises a bore in communication with the harvester cavity and extending the longitudinal length of the harvester.

14. The assembly of claim 7, further comprising a plunger disposed within at least the harvester cavity for dislodging the bone plug therefrom.

15. A surgical assembly according to claim 14, wherein the havester is removably disposed within the cutting element.

16. A surgical assembly according to claim 15, wherein the havester is slidably disposed within the cutting element.

17. A surgical assembly according to claim 7, wherein the bone plug removal tool comprises an anvil engaged at a distal end thereof for transmitting a driving force to the cutting element.

18. A surgical assembly according to claim 17, wherein the anvil is removably mounted to a distal end of the harvester.

19. A surgical assembly according to claim 17, wherein the anvil includes a stem concentrically mounted within a harvester bore for radially securing the anvil to the tool.

20. A surgical assembly according to claim 19, further comprising a buffer of resilient material located between the anvil and the harvester.

21. A bone plug remover comprising an outer element having a cutting portion disposed at a proximal end thereof for cutting a plug from a bone, an inner element having a receiving portion, substantially aligned with the cutting portion of the first element, for receiving the plug cut thereby, the inner element being removably disposed within the outer element.

22. A method of repairing a defective articular cartilage, comprising removing a plug from bone with the bone plug remover of claim 21, disengaging the inner element of that bone plug remover from the outer element, positioning the receiving portion of the inner element substantially adjacent a bone hole and disgorging the plug from the inner element into that hole.

23. A method according to claim 22, comprising the step of disgorging the plug into the hole by pushing the plug with a plunger.

24. A method according to claim 23, comprising the steps of forming the hole in the bone at a site of articular cartilage damage, cutting the plug from the bone at a site that is substantially free of such damage, and placing the plug into the hole so that articular cartilage affixed to the plug is coextensive with, and in lateral registration with, articular cartilage external to the hole at the site of cartilage damage.

* * * * *